(12) United States Patent
Pedicini

(10) Patent No.: US 11,076,903 B2
(45) Date of Patent: *Aug. 3, 2021

(54) ORTHOPEDIC DEVICE DELIVERING A CONTROLLED, REPEATABLE IMPACT

(71) Applicant: DePuy Synthes Products, Inc., Raynham, MA (US)

(72) Inventor: Christopher Pedicini, Franklin, TN (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/600,234

(22) Filed: May 19, 2017

(65) Prior Publication Data

US 2018/0055553 A1 Mar. 1, 2018

Related U.S. Application Data

(63) Continuation of application No. 15/446,862, filed on Mar. 1, 2017, which is a continuation-in-part of application No. 15/439,692, filed on Feb. 22, 2017, now Pat. No. 10,603,050.

(60) Provisional application No. 62/393,975, filed on Sep. 13, 2016, provisional application No. 62/381,864, filed on Aug. 31, 2016.

(51) Int. Cl.
*A61B 17/92* (2006.01)

(52) U.S. Cl.
CPC ........ *A61B 17/92* (2013.01); *A61B 2017/925* (2013.01); *A61B 2017/928* (2013.01)

(58) Field of Classification Search
None
See application file for complete search history.

(56) References Cited

U.S. PATENT DOCUMENTS

| 4,468,594 A | 8/1984 | Jacquemet |
| 5,057,112 A | 10/1991 | Sherman et al. |
| 5,108,400 A | 4/1992 | Appel et al. |

(Continued)

FOREIGN PATENT DOCUMENTS

| JP | 2004130471 A | 4/2004 |
| WO | 2016/112397 A1 | 7/2016 |

OTHER PUBLICATIONS

International Search Report and Written Opinion issued in PCT/US2017/020218 dated Jun. 8, 2017.

(Continued)

*Primary Examiner* — Samuel S Hanna

(57) ABSTRACT

A motor-driven orthopedic impacting tool is provided for orthopedic impacting in the hips, knees, shoulders and the like. The tool is capable of holding a broach, chisel, or other end effector, which when gently tapped in a cavity with controlled percussive impacts, can expand the size or volume of an opening of the cavity or facilitate removal of the broach, implant, or other surgical implement from the opening. A stored-energy drive mechanism stores potential energy and then releases it to launch a launched mass or striker to communicate a striking force to an adapter in either a forward or reverse direction. The tool may further include a combination anvil and adapter and an energy adjustment mechanism to adjust the striking force the launched mass delivers to the adapter in accordance with a patient profile.

17 Claims, 11 Drawing Sheets

(56) References Cited

U.S. PATENT DOCUMENTS

| | | | | |
|---|---|---|---|---|
| 5,992,538 | A | * | 11/1999 | Marcengill .......... B25D 11/102 |
| | | | | 173/171 |
| 6,199,640 | B1 | * | 3/2001 | Hecht .................... B25D 16/00 |
| | | | | 173/109 |
| 6,387,113 | B1 | * | 5/2002 | Hawkins .............. A61B 17/064 |
| | | | | 227/180.1 |
| 6,875,220 | B2 | | 4/2005 | Du et al. |
| 6,938,705 | B2 | | 9/2005 | Kikuchi |
| 8,602,124 | B2 | | 12/2013 | Pedicini |
| 8,695,726 | B2 | | 4/2014 | Pedicini |
| 8,936,105 | B2 | | 1/2015 | Pedicini |
| 9,539,714 | B1 | | 1/2017 | Pedicini |
| 9,901,354 | B2 | | 2/2018 | Pedicini |
| 9,950,417 | B2 | * | 4/2018 | Ito .............................. B25F 5/00 |
| 9,962,821 | B2 | | 5/2018 | Pedicini et al. |
| RE46,954 | E | | 7/2018 | Pedicini |
| RE46,979 | E | | 8/2018 | Pedicini |
| 10,065,300 | B2 | | 9/2018 | Pedicini |
| 10,603,050 | B2 | | 3/2020 | Pedicini |
| 10,751,865 | B2 | | 8/2020 | Pedicini et al. |
| 2004/0026097 | A1 | | 2/2004 | Hecht |
| 2005/0101962 | A1 | * | 5/2005 | Schwenke ............ A61F 2/4607 |
| | | | | 606/86 R |
| 2005/0247462 | A1 | | 11/2005 | Meixner et al. |
| 2008/0245541 | A1 | | 10/2008 | Grunig |
| 2009/0236387 | A1 | * | 9/2009 | Simonelli ............. B25C 5/1668 |
| | | | | 227/8 |
| 2009/0266570 | A1 | | 10/2009 | Hashimoto et al. |
| 2010/0137760 | A1 | | 6/2010 | Schulz et al. |
| 2012/0215267 | A1 | | 8/2012 | Pedicini |
| 2013/0161050 | A1 | * | 6/2013 | Pedicini ................. B25D 17/00 |
| | | | | 173/201 |
| 2014/0318819 | A1 | | 10/2014 | Pedicini |
| 2015/0196343 | A1 | | 7/2015 | Donald et al. |
| 2015/0289886 | A1 | * | 10/2015 | Kfir .................... A61B 17/1604 |
| | | | | 606/84 |
| 2016/0096259 | A1 | * | 4/2016 | Pedicini ................. B25C 1/047 |
| | | | | 227/146 |
| 2016/0199199 | A1 | | 7/2016 | Pedicini |
| 2017/0042692 | A1 | * | 2/2017 | Stewart .................. A61B 17/92 |
| 2017/0196701 | A1 | | 7/2017 | Behzadi et al. |
| 2018/0055518 | A1 | | 3/2018 | Pedicini |
| 2018/0055552 | A1 | | 3/2018 | Pedicini |
| 2018/0055554 | A1 | | 3/2018 | Pedicini |
| 2020/0197028 | A1 | | 6/2020 | Pedicini |

OTHER PUBLICATIONS

International Search Report and Written Opinion dated May 29, 2017 in PCT/US2017/018921.

U.S. Appl. No. 16/795,942, filed Feb. 20, 2020, Christopher Pedicini.

Yanoso-Scholl et al.; A Novel Test Method to Characterize Intraoperative Impacts During Femoral Broaching and Stem Insertion, ORS 2012 Annual mtg. (1 page).

* cited by examiner

ORTHOPEDIC DEVICE DELIVERING A CONTROLLED, REPEATABLE IMPACT

CROSS-REFERENCE TO RELATED APPLICATIONS

The present application is a continuation of U.S. patent application Ser. No. 15/446,862 filed Mar. 1, 2017, which is a continuation-in-part of U.S. patent application Ser. No. 15/439,692 filed Feb. 22, 2017, and also claims the benefit of 35 USC § 119 to U.S. Provisional Patent Application No. 62/393,975 filed Sep. 13, 2016, and U.S. Provisional Patent Application No. 62/381,864 filed Aug. 31, 2016, the entire contents of each of which are incorporated by reference herein.

FIELD OF THE DISCLOSURE

The present disclosure relates to locally powered tools for impacting in surgical applications such as orthopedic procedures, and, more particularly, to a hand-held motor driven tool for bidirectional, surgical impacting that is driven by a launched mass to provide controlled, repeatable impacts to a broach or other end effector.

BACKGROUND

In the field of orthopedics, prosthetic devices, such as artificial joints, are often implanted or seated in a patient's bone cavity. The cavity is typically formed during surgery before a prosthesis is seated or implanted, for example, a physician may remove and or compact existing bone to form the cavity. The prosthesis usually includes a stem or other protrusion that is inserted into the cavity.

To create the cavity, a physician may use a broach conforming to the shape of the stem of the prosthesis. Solutions known in the art include providing a handle with the broach for manual hammering by the physician during surgery to impel the broach into the implant area. Unfortunately, this approach is crude and notoriously imprecise, leading to unnecessary mechanical stress on the bone. The results can be unpredictable and depend on the skill of a particular physician. Historically, this approach will in many cases result in inaccuracies in the location and configuration of the cavity. Additionally, the surgeon is required to expend an unusual amount of physical force and energy to hammer the broach and to manipulate the bones and prosthesis. Most importantly, this approach carries with it the risk that the physician will cause unnecessary further trauma to the surgical area and damage otherwise healthy tissue, bone structure and the like.

Another technique for creating the prosthetic cavity is to drive the broach pneumatically, that is, by compressed air. This approach is disadvantageous in that it prevents portability of an impacting tool, for instance, because of the presence of a tethering air-line, air being exhausted from a tool into the sterile operating field and fatigue of the physician operating the tool. This approach, as exemplified in U.S. Pat. No. 5,057,112 does not allow for precise control of the impact force or frequency and instead functions very much like a jackhammer when actuated. Again, this lack of any measure of precise control makes accurate broaching of the cavity more difficult and can lead to unnecessary patient complications and trauma.

A third technique relies on computer-controlled robotic arms for creating the cavity. While this approach overcomes the fatiguing and accuracy issues, it suffers from having a very high capital cost and additionally removes the tactile feedback that a surgeon can get from a manual approach.

A fourth technique relies on the inventor's own, previous work which uses a linear compressor to compress air on a single stroke basis and then, after a sufficient pressure is created, to release the air through a valve and onto a striker. This then forces the striker to travel down a guide tube and impact an anvil, which holds the broach and or other surgical tool. However, this arrangement, due to the pressure of the air, results in the generation of large forces on the gear train and linear motion converter components, which large forces lead to premature wear on components.

A fifth technique also relies on the inventor's own, previous work which uses a linear actuator to create a vacuum against a detent. After a sufficient vacuum volume is generated, the detent releases a striker and allows the striker to travel down a guide tube and impact an anvil, which holds a broach or other surgical tool. This arrangement, however, puts undue stress on the drive components and is subject to environmental conditions, such as the atmospheric pressure. Furthermore, this technique is limited in its ability to generate a reverse or rearward impact.

Consequently, there exists a need for an impacting tool having an improved drive assembly that overcomes the various disadvantages of existing systems and previous solutions of the inventor.

SUMMARY

In view of the foregoing disadvantages, an electric motor-driven orthopedic impacting tool is provided for orthopedic impacting in hips, knees, shoulders and the like. The tool is capable of holding a broach, chisel, or other end effector and gently tapping the broach, chisel or other end effector into the cavity with controlled percussive impacts, resulting in a better fit for the prosthesis or the implant. Further, the control afforded by such an electrically manipulated broach, chisel, or other end effector allows adjustment of the impact settings according to a particular bone type or other profile of a patient. The tool additionally enables proper seating and in the case of bidirectional movement the removal of the prosthesis or the implant into or out of an implant cavity and advantageously augments the existing surgeon's skill in guiding the instrument.

In an exemplary embodiment, an electric motor-driven orthopedic impacting tool comprises a local power source (such as a battery or fuel cell), a motor, a controller, a housing, a method of converting rotary motion to linear motion (hereafter referred to as a linear motion converter), a stored-energy drive system or mechanism such as a gas or mechanical spring capable of storing and releasing potential energy, and a striker energized by the stored-energy drive system to be operational in a forward and/or a rearward direction, where the striker is capable of generating an impact force to a surgical implement. The tool may further deliver focused illumination to the surgery area by way of a semiconductor light source, such as an LED, or traditional incandescent light source. A handle may be provided for handling the tool by a physician, or a suitable mount interface for integrating the tool into a robotic assembly. A local power source such as a battery is also included. As is typical, at least some of the various components are preferably contained within a housing. The tool is capable of applying cyclic, repeatable impact forces on a broach, chisel, or other end effector, or an implant. Given the repeatability of the impact force, finely tuning the impact force to a plurality of levels is also contemplated. To this end a plurality of springs may be provided together with the device in a kit format, whereby different visually-coded springs may be removably introduced to the tool as needed during a surgical procedure to provide for a range of drive forces.

Regarding the stored-energy drive system, the system is preferably actuatable by a motor and gearbox in combination with a cam, which rotates in a first direction compressing a spring, thus storing potential energy within the stored-energy drive system. The cam further continues to rotate and releases the stored energy, which, in turn, can accelerate a mass to generate a forward impact. As an example, after sufficient displacement of a mechanical spring or gas spring, in which stored potential energy is increased, the cam continues to rotate until it moves past a release point where it ceases to act on the mass, releasing the stored energy. Upon release, the stored potential energy accelerates a mass in the forward direction until it comes into operative contact with the point of impact, such as the anvil or another impact surface. Conversely, for a bidirectional impacting system the cam can alternatively rotate in an opposite, second direction, compressing a spring, again storing potential energy within the spring storage system. The cam further continues to rotate to a release point where it ceases to act on the spring storage system and the spring storage system can release the stored energy, which, in turn, can accelerate a mass to generate a rearward impact. As an example, after sufficient displacement of the spring, in which stored potential energy of the spring is increased, the cam continues to rotate until it moves past a release point where it ceases to act on the mass, releasing the stored-energy drive system (or mechanism). Upon release, the potential energy in the stored-energy drive system accelerates a mass in the opposite, rearward direction until it comes into operative contact with the point of impact, such as the anvil or another impact surface.

In an exemplary embodiment, the launched mass (which can incorporate part or all of the stored-energy drive system) separates from a pusher plate or pushing surface prior to its point of impact. Accordingly, in this embodiment, since the entire stored-energy drive system is the launched mass, very high efficiencies were unexpectedly achieved. In a further embodiment which uses a mechanical spring, the compression ratio of the spring is less than about 50% of its free length, and more preferably, less than 40% of its free length. The inventor has found that such compression ratios increase the consistency of the impact energy delivered and reduce the likelihood of permanent spring deformation.

In a further exemplary embodiment, the handle may be repositionable or foldable back to the tool to present an inline tool wherein the surgeon pushes or pulls on the tool co-linearly with the direction of the broach. This has the advantage of limiting the amount of torque the surgeon may put on the tool while it is in operation. In a further refinement of the hand grip, there may be an additional hand grip for guiding the surgical instrument and providing increased stability during the impacting operation. In a still further embodiment, the tool may be attached to a robot thus eliminating the need for a handle and the tool may use a tethered or remote power source.

In a further exemplary embodiment, the adapter, broach, chisel or other end effector can be rotated to a number of positions while still maintaining axial alignment, as illustrated, for example, in FIG. 9, where the adapter is rotatable in four different positions, each position rotated by 90°. This facilitates the use of the adapter or broach, for example, in various anatomical presentations during surgery.

In an exemplary embodiment, an anvil of the tool includes at least one of two points of impact, a forward striking surface or first surface and a rearward striking surface or second surface, and a guide assembly, such as guide rollers, bearings, or Polytetrafluoroethylene (PTFE) or Teflon tracks to constrain the striker to move in a substantially axial direction. The point of impact of the striker and the resulting force on the surgical tool can be both in the forward and reverse directions. In the bidirectional impacting operation, when a forward force on the surgical tool is generated, the striker moves along the guide assembly and continues in the forward direction. A reversing mechanism can be used to change the point of impact of the striker and the resulting force on the surgical tool. Use of such a reversing mechanism results in a rearward force being exerted on the anvil and/or the broach or other surgical attachment. As used in this context, "forward direction" connotes movement of the striker toward a broach, chisel or patient, and "rearward direction" connotes movement of the striker away from the broach, chisel or patient. The selectivity of either bidirectional or unidirectional impacting provides flexibility to a surgeon in either cutting or compressing material within the implant cavity in that the choice of material removal or material compaction is often a critical decision in a surgical procedure, as discussed, for example, in U.S. Pat. No. 8,602,124. Furthermore, it was discovered in the use of the inventor's own, previous work that the tool could be used in a broader range of surgical procedures if the reverse impact force could be approximately equal to the forward impact force. In an embodiment the forward and rearward forces impact at least two separate and distinct points.

In an exemplary embodiment the anvil and the adapter comprise a single element, or one may be integral to the other.

In typical impactors, as shown in U.S. Pat. No. 6,938,705, as used in demolition work, varying the speed varies the impact force, making it impossible to maintain constant impact energy, defined as +/−20%, in variable speed operation. Accordingly, in an exemplary embodiment, the tool comprises a control element or controller, which includes an energy adjustment element or mechanism, and which energy adjustment element may control the impact force of the tool by controlling storage and release of energy output from the stored-energy drive mechanism. The energy may be regulated electronically or mechanically (see switch 34 in FIG. 9, for example). Furthermore, the energy adjustment element may be analog or have fixed settings. This control element allows for the precise control of the impacting operation. The energy adjustment element allows a surgeon to increase or decrease the impact energy of the tool according to a patient's profile.

In a further exemplary embodiment, the tool is also capable of controlling the frequency of the striker's impacting movement, using, for example, a mechanical switch 36 illustrated in FIG. 9. By regulating the frequency of the striker, the tool may, for example, impart a greater total time-weighted percussive impact, while maintaining the same impact magnitude. This allows the surgeon better control over the cutting speed of the broach or chisel. For example, the surgeon may choose cutting at a faster rate (higher frequency impacting) during the bulk of the broach or chisel movement and then slow the cutting rate as the broach or chisel approaches a desired depth. In fact, during testing of the tool, it was discovered that a higher frequency impacting rate, such as 3 impacts per second, preferably up to 10 impacts per second, coupled with a constant energy per impact, such as between 2 to 6 joules per second, preferably up to 40 joules per second, allowed the surgeon to better position certain surgical implements. This was seen, for example, in the seating of an acetabular cup, where an impact frequency of at least 3 impacts per second, at an energy of between 2 and 6 joules per second, resulted in far better control of the position of the acetabular cup over the prior manual hammering technique.

In an exemplary embodiment, the stored-energy drive mechanism, or energy storage and release mechanism, defines points of operation, either mechanically or electrically. As a result, the energy per impact is delivered in accordance with the selected points of operation. In fact, the energy per impact can be controlled to better than 20%. In a further embodiment, timing elements may be incorporated into the system such that the impact is delivered at predetermined frequencies, selectable by the user. Using the electronic control element or controller and precisely controlling the rate of impact allows the surgeon to control the total energy delivered by the tool.

In an exemplary embodiment the direction of impacting is controlled by a biasing force placed by a user on the tool and detected by a sensor, such as a positioner sensor, on the anvil. For example, biasing the tool in the forward direction results in the launched mass being launched forward and gives forward impacting, whereas biasing the tool in the rearward direction results in the launched mass being launched rearward and gives rearward impacting.

In an exemplary embodiment the tool may have a lighting element to illuminate a work area and accurately position the broach, chisel, or other end effector on a desired location on the prosthesis or the implant.

In an exemplary embodiment a bumper is predisposed between a head of the piston and an end of the striker, reducing the impact stress and prolonging the life of the entire assembly.

In an exemplary embodiment the tool may also include a feedback system that warns the user when a bending or off-line orientation beyond a certain magnitude is detected at a broach, chisel, or other end effector or implant interface or the orthopedic implement is not advancing.

In an exemplary embodiment the tool may further allow for a replaceable cartridge to vary the impact forces. These cartridges could be rated by the total energy delivered by the stored energy system when actuated by the linear motion converter. As an example, a low power cartridge with a limit in the range of 2 to 3 joules or less could be used for soft or osteoporotic bone. In the case of young, hard bone, a power cartridge with impact energy of 4 or more joules could be selected. By allowing for a variety of cartridges, which in an embodiment could be visually coded according to power, the surgeon would have flexibility in determining the impact energy per cycle by simply selecting the appropriate power cartridge provided with the tool in a kit.

These together with other aspects of the present disclosure, along with the various features of novelty that characterize the present disclosure, are pointed out with particularity in the claims annexed hereto and form a part of the present disclosure. For a better understanding of the present disclosure, its operating advantages, and the specific non-limiting objects attained by its uses, reference should be made to the accompanying drawings and detailed description in which there are illustrated and described exemplary embodiments of the present disclosure.

BRIEF DESCRIPTION OF THE SEVERAL VIEWS OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

A motor-driven orthopedic impacting tool is provided with controlled percussive impacts. The motor may be electric, such as a brushless, autoclavable motor such as those generally available from Maxon Motor® and/or Portescap®. The tool includes the capability to perform single and multiple impacts, as well as impacting of variable and varying directions, forces, and frequencies. In an embodiment the impact energy is adjustable. In another embodiment the impact is transferred to a broach, chisel, or other end effector connected to the tool.

The tool further includes a housing. The housing may securely cover and hold at least one component of the tool and is formed of a material suitable for surgical applications, such as aluminum or Polyphenylsulfone (PPSF or PPSU), also known as Radel®. In an embodiment, the housing contains a motor, at least one reducing gear, a linear motion converter, a spring element which is preferably a mechanical or gas spring, a striker or launched mass, a control circuit or module, an anvil, a first or forward striking surface for forward impact, and a different, second or rearward striking surface for rearward impact.

The tool further may include a handle portion with an optional hand grip for comfortable and secure holding of the tool, or a suitable mount interface for integrating the tool into a robotic assembly while in use, and an adapter, a battery, a positional sensor, a directional sensor, and a torsional sensor. The tool may further deliver focused illumination by way of a semiconductor light source, such as an LED, or traditional incandescent light source to provide light in the surgical work area in which a surgeon employs the tool. The anvil may be coupled to a broach, chisel or other end effector known in the art through the use of an interfacing adapter, which adapter may have a quick connect mechanism to facilitate rapid change of different broaching sizes. The anvil may further include a locking rotational feature to allow the tool to be positioned in different fashions as to gain tissue clearance to tool features such as the handle.

In a further embodiment, an axis of the launched or thrown mass is preferably aligned axially, along the direction of movement, to within 20 degrees of the axis of the adapter, and more preferably, to within 10 degrees of the axis of the adapter. Such axial alignment is important in terms of maximizing the energy transferred to the surgical implement, as well as minimizing the generation of off-axis forces, which can contribute to adverse surgical outcomes, such as fractures.

Figure 1:
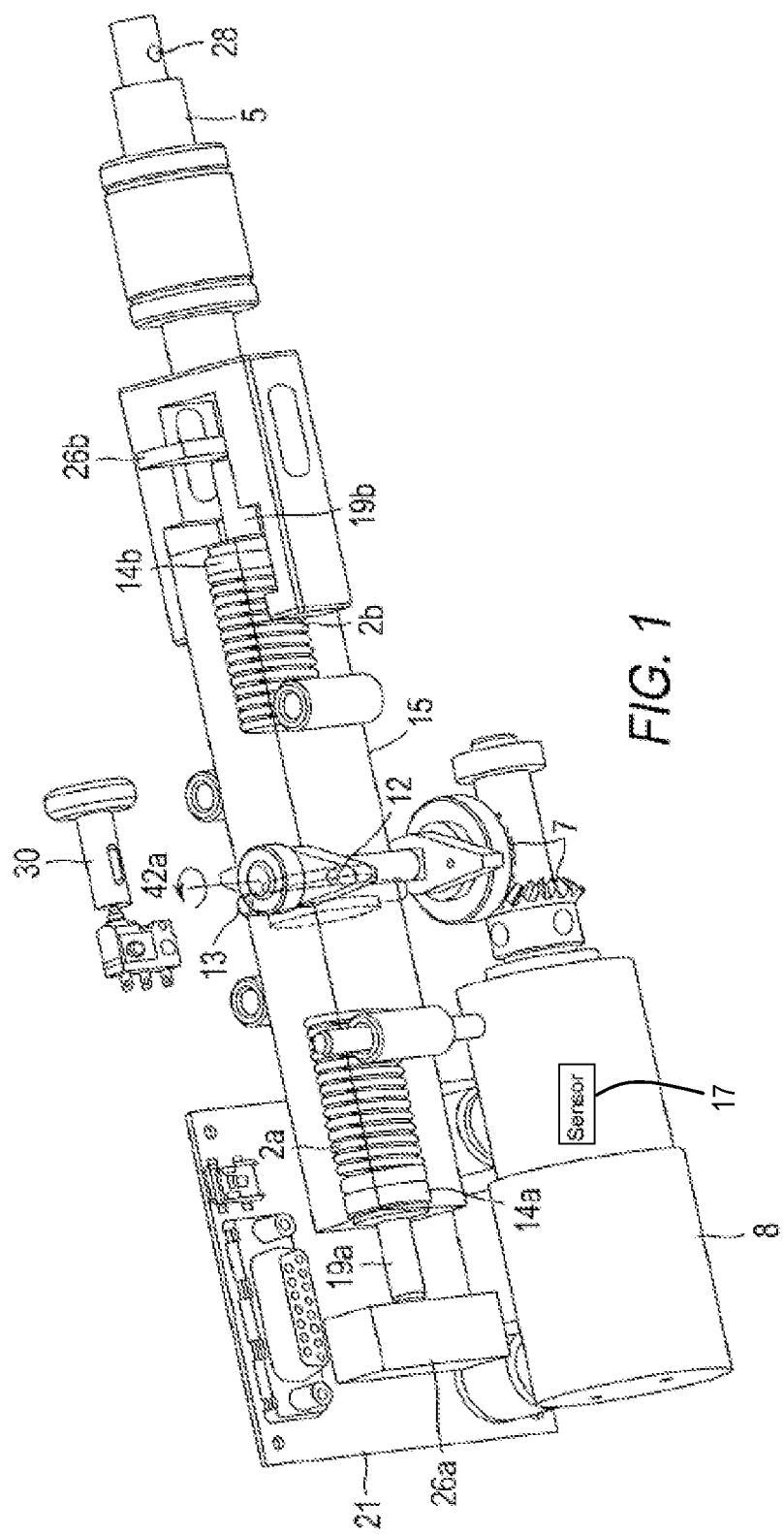
FIG. 1 illustrates a perspective view of an orthopedic impacting tool in accordance with an exemplary embodiment of the present disclosure in which a mechanical spring assembly system is used for generating a forward impact force.

Referring now generally to FIGS. 1 through 7, in an exemplary embodiment, a bidirectional impact force may be generated using a mechanical spring assembly system, as illustrated, for example, in FIG. 1. Alternatively, a single mechanical spring assembly may be used. FIG. 1 shows a perspective view of an orthopedic impacting tool in accordance with an embodiment of the present disclosure in which a motor and gearbox 8 of the mechanical spring assembly system, in combination with a linear motion converter, which includes a cam 12 and a cam follower 13, actuates a first spring piston 19*a* (hereinafter referred to as the "first piston 19*a*") and/or a launched mass or striker 15, in order to ultimately generate a forward impact force. It is to be noted that the piston generally refers to a thrusting or push off element and can have any of a number of shapes. The cam 12 is shown as having a symmetrical profile, a dual wedge shape, but the design contemplates that any shape may be used which provides a quick release of the spring. Alternative ways for actuating and quickly releasing the spring include, but are not limited to, using an interrupted rack and pinion or a climbing mechanism. The spring assembly system further includes, among other components, reducing gears 7 and an anvil 5. The first piston 19*a* engages a first spring 2*a*, which can be either a mechanical or gas spring. In the mechanical spring assembly system, the deflection in relation to a free length of the spring is preferably less than 50%. Music wire or, more preferably, stainless steel or titanium are suitable materials for the spring. Preferably, the spring is a compression spring, although other types of springs are contemplated. In the gas spring assembly system, the gas spring operates under pressure in a range of about 100 to 3000 psi, for example. The gas spring is preferably initially charged with a non-oxidizing gas, such as nitrogen, or an inert gas, such as argon. One of the advantages of using nitrogen can include a lower permeation rate through seals of the gas spring, resulting in a potentially longer shelf life for the seals and the spring itself.

Figure 2:
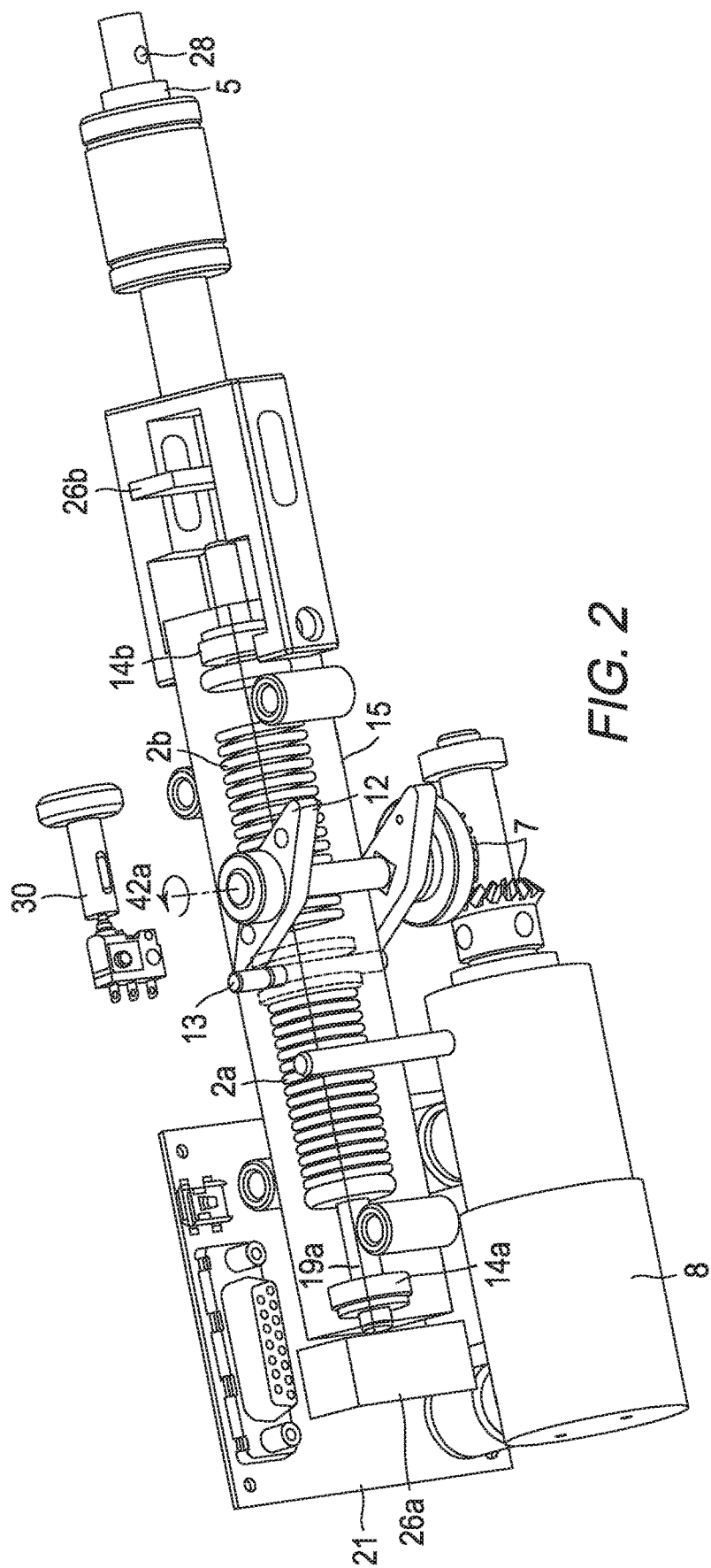
FIG. 2 shows an exemplary embodiment of the tool in FIG. 1 in which the cam positions the piston in the operative position for release for a forward impact.
Figure 3:
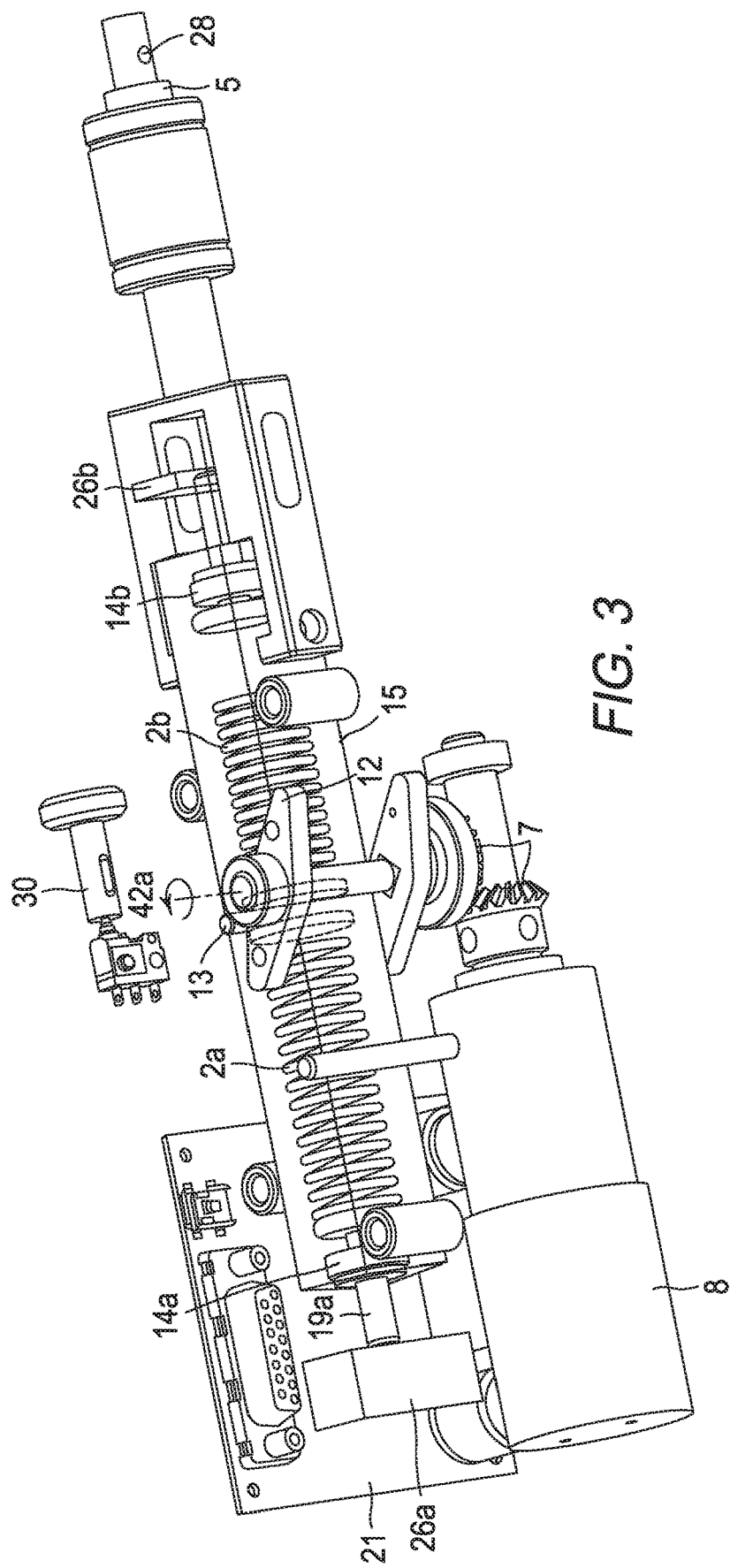
FIG. 3 shows an exemplary embodiment of the tool in FIG. 1 in which after the stored-energy has been released, a launched mass is accelerated towards a point of impact in a forward direction.

FIG. 2 is an exemplary embodiment of the tool in FIG. 1 in which the cam 12 used for actuating the first piston 19*a* has the first piston 19*a* "cocked" in the operative position ready for release, or stated another way, the motor 8 rotates the cam 12 in a first direction (viewed as counterclockwise for tautological purposes), as shown by arrow 42*a*, and compresses the first piston 19*a* against a first pusher plate 26*a*, thus storing potential energy within the first spring 2*a*. In the "cocking phase" the first piston 19*a*, in combination with the launched mass or striker 15, contacts and is pushed by the cam follower 13, which is driven by the cam 12 in the first direction. As the cam 12 continues to rotate in the first direction, energy stored inside the first spring 2*a* increases until the cam 12 moves past a release point where it ceases to act on the striker 15 (see FIG. 3, for example). The striker (or launched mass) 15 is now free to travel under the stored potential energy of the first spring 2*a*. In particular, after a sufficient displacement of the first piston 19*a*, and after the cam 12 releases the first piston 19*a* and/or the launched mass 15 combination, the first piston 19*a* moves in a forward direction, i.e., a direction toward the point of impact, and, at the same time, accelerates the launched mass or striker 15, which is in contact with the face of the first piston 19*a*. As shown, for example, in FIG. 3, the first piston 19*a* releases from the striker 15, launching it towards the anvil 5. It was unexpectedly discovered in this invention that the release of the striker 15 from the pusher plate 26*a*, which essentially creates a portion of free flight during its travel, dramatically reduces the recoil generated and experienced by the surgeons' hands, resulting in a more controllable tool. The striker 15, which has been launched towards the end of the tool that is proximate to the end effector or patient, then percussively impacts a first surface or forward striking surface of the anvil 5, where a maximum displacement of the anvil when in contact with the striker is less than 15 mm. It was unexpectedly discovered during testing of the tool that surgeons achieved better results, in terms of more precise and accurate movements, when a maximum forward displacement of the anvil was limited to less than 15 mm, and more preferably, less than 10 mm. By limiting the stroke, the resulting surgical procedure was more accurately executed and in better alignment with the surgical target, as compared to larger strokes. In stark contrast, use of a mallet during surgery, for example, often leads to displacements of 20 mm or more, resulting in less accuracy during the procedure.

The impact of the striker 15 on the anvil 5 communicates a forward impact force to an adapter 1 and thereby to the broach, chisel, or other orthopedic instrument. The launched mass or striker 15 may be constructed from a suitable material such as steel or any other material having similar properties, lending it to repeated impacting. In an embodiment, a ratio of a weight or mass of the launched mass or striker 15 to a weight or mass of the tool is preferably less than 25%, and the launched mass 15 has an amount of free flight before contact, both factors contributing to a further reduction in the recoil generated.

In a further embodiment it was unexpectedly discovered by increasing the weight or mass of the launched mass in relation to the weight or mass of the anvil that the impact energy was more effectively transferred to the surgical implement. For example, when a ratio of the mass of the launched mass to the mass of the anvil is less than 25%, the resultant transfer efficiency is extremely low, i.e., less than 50% for a typical coefficient of restitution of 0.8. As such, it was found that mass ratios under 50% resulted in the lowest transfer efficiencies of the impact.

In a further embodiment, as illustrated in FIG. 2, for example, as the striker 15 moves in the rearward direction, towards the pusher plate 26*a*, a bumper 14*a* functions as a stopper to prevent an end face of the piston 19*a* from impacting the striker 15. The bumper 14*a* absorbs the impact of the piston 19*a* immediately before the launched mass or striker 15 is launched in the forward direction. It was discovered in the course of the invention that without having the piston 19a come to rest on the bumper 14a, excessive wear occurred resulting in failure of the piston 19a. Accordingly, such bumper 14a prevents damage to the spring assembly system, particularly the piston 19a, during repeated operation. The bumper 14a can be one of a plastic or more preferably a rubber or urethane material.

As discussed above, it has been determined by the inventor that his previous designs occasionally resulted in the surgical implement seizing in a biological cavity and the impact of the striker 15 in the rearward direction may be insufficient to dislodge the tool. Further, it was discovered that the rearward force needs to be communicated as a sharp retracting impact in order to dislodge the surgical implement. Accordingly, in the present bidirectional impacting system, there are at least two different impacting surfaces, and, when the tool is being pulled away from the cavity, the striker 15 will impact an alternate surface on the anvil 5 and thereby communicate a rearward force on the anvil 5.

Figure 4:
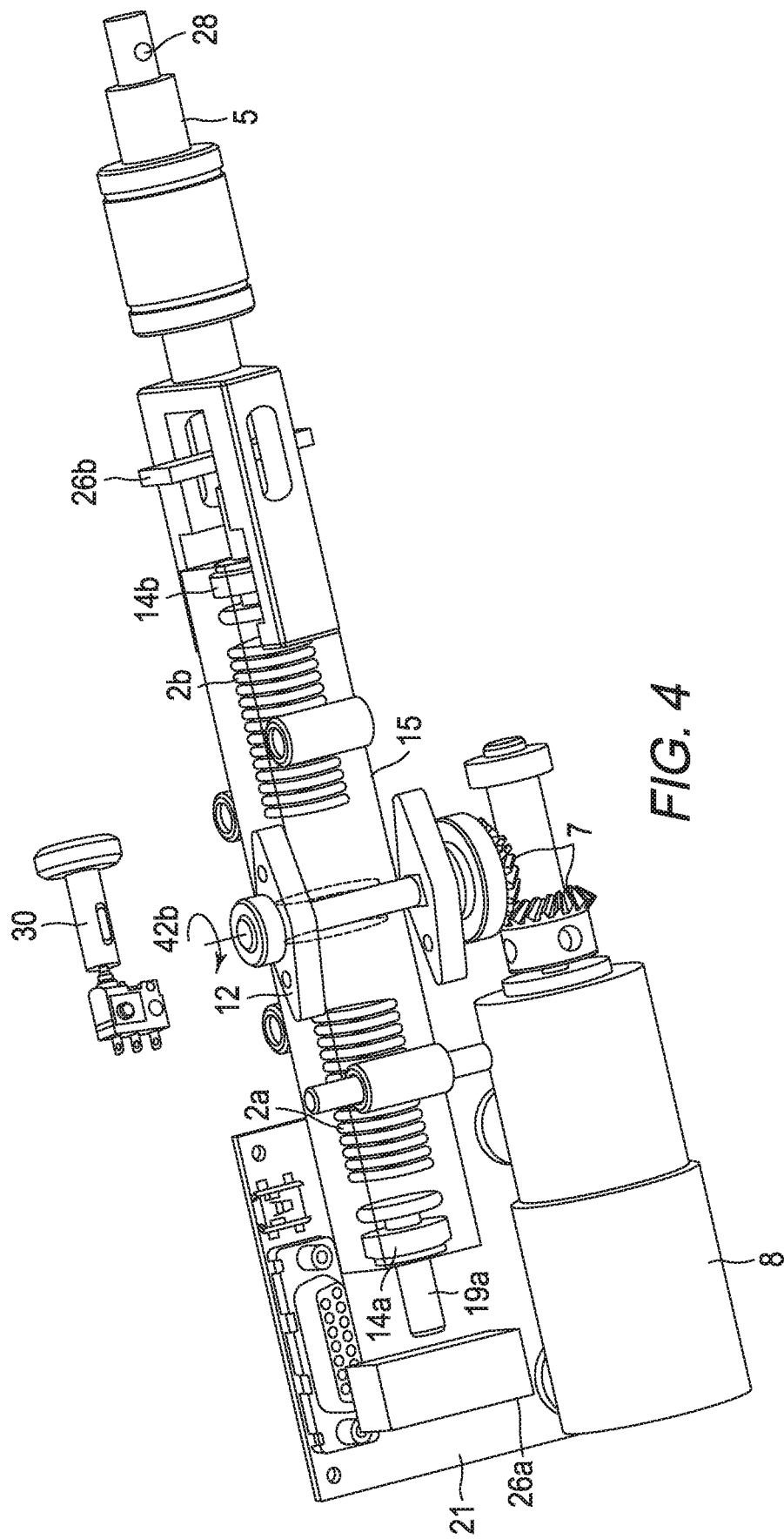
FIG. 4 illustrates a perspective view of an orthopedic impacting tool in accordance with an exemplary embodiment of the present disclosure in which a mechanical spring is used for generating a rearward impact force.
Figure 5:
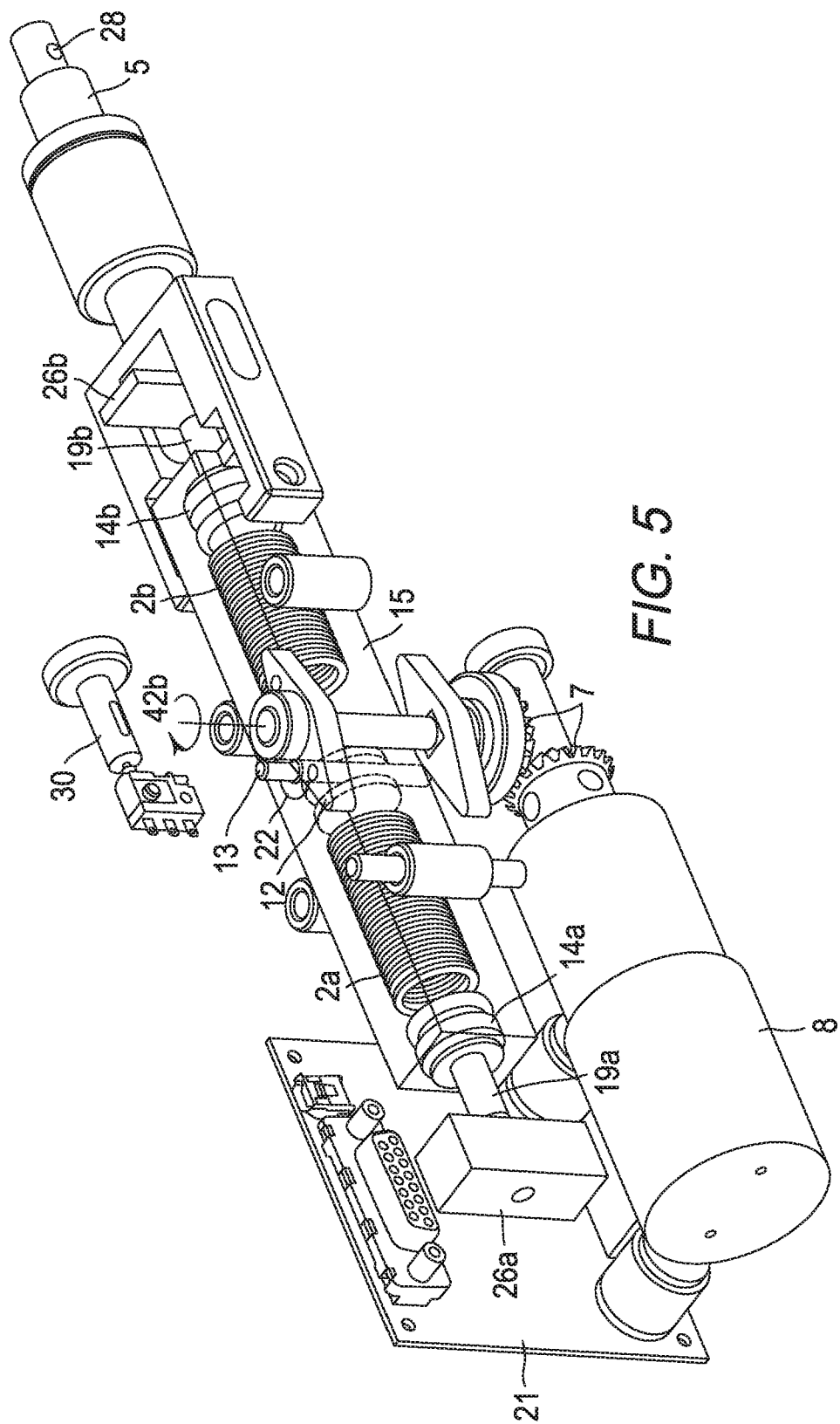
FIG. 5 shows another perspective view of the impacting tool in FIG. 4 from an alternate angle.
Figure 6:
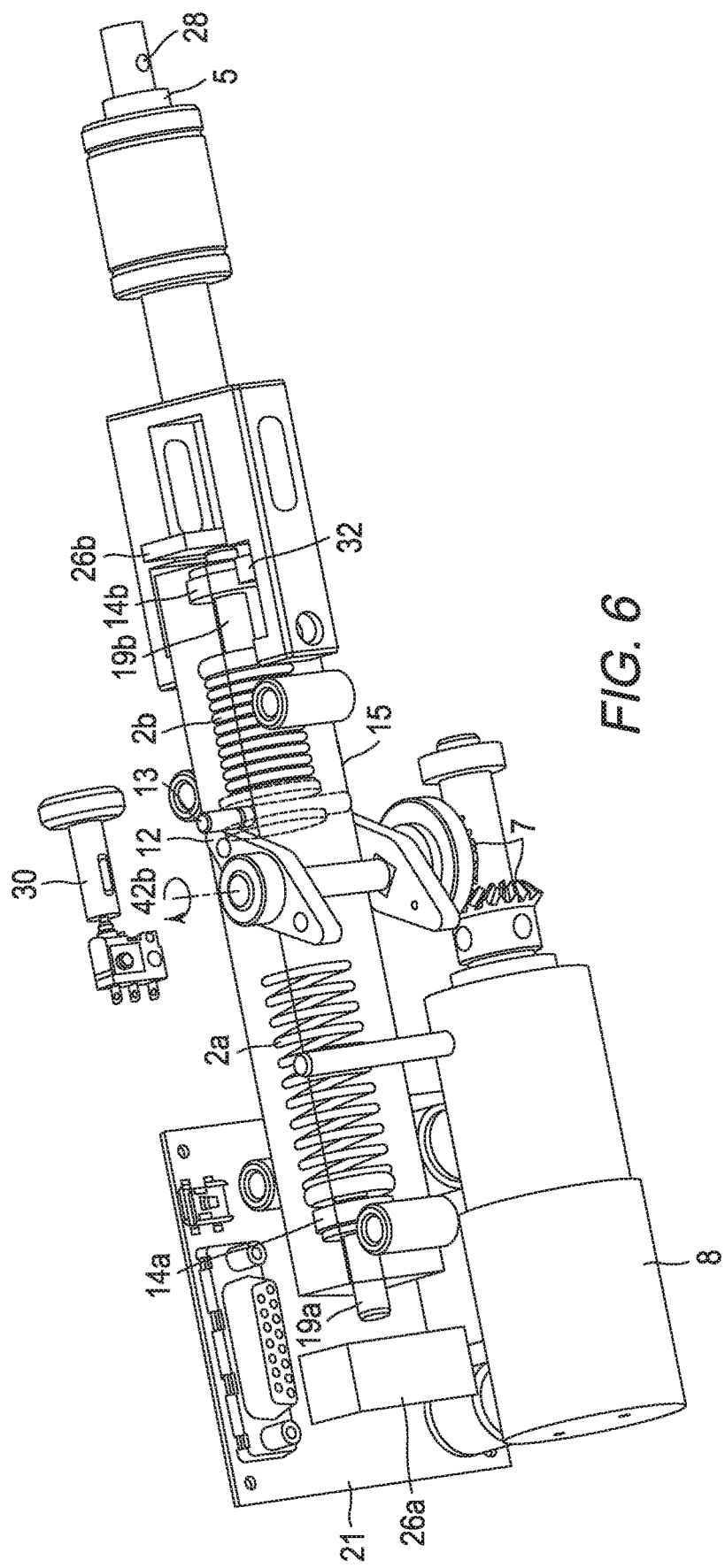
FIG. 6 shows an exemplary embodiment of the tool in FIG. 4 in which the cam of the mechanical spring positions piston in the operative position for release for a rearward impact.
Figure 7:
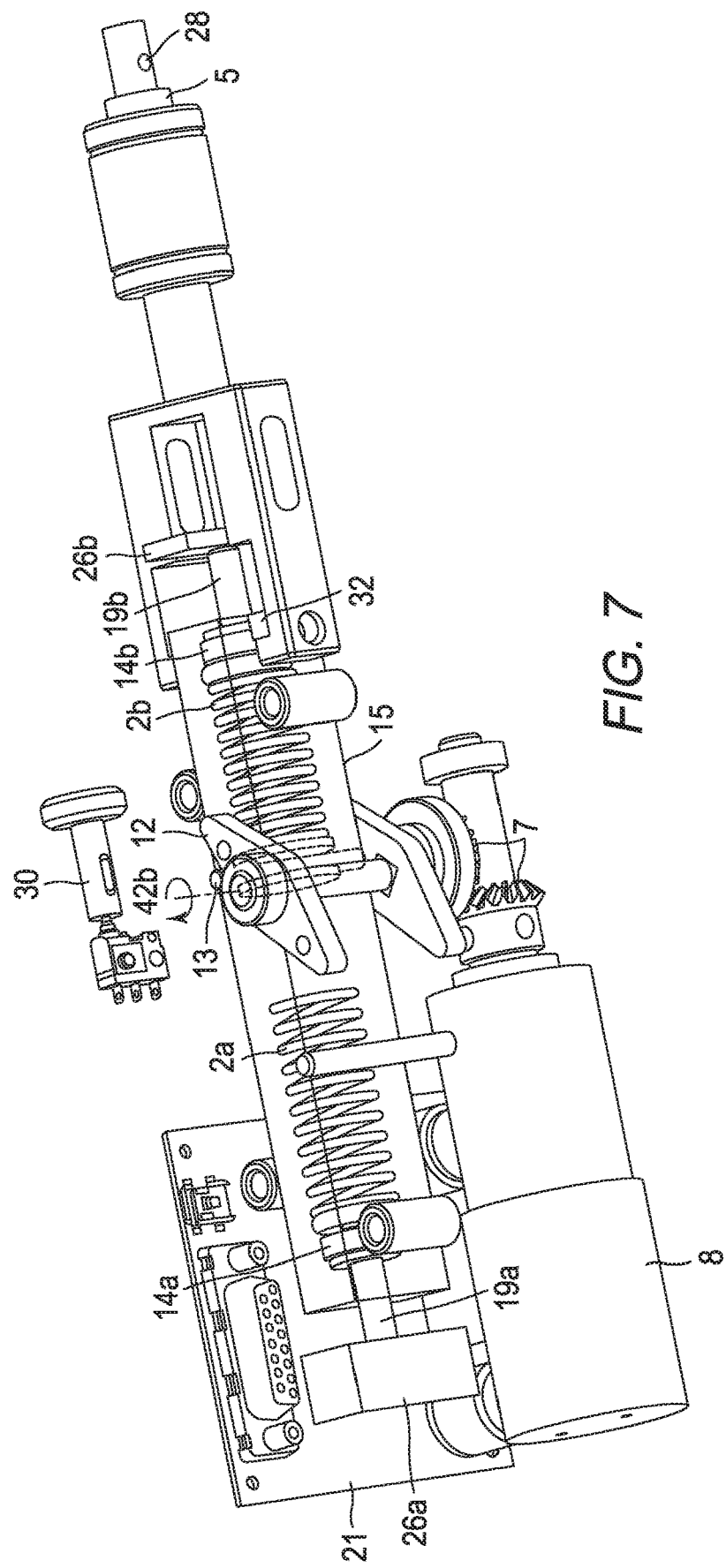
FIG. 7 shows an exemplary embodiment of the tool in FIG. 4 in which after the spring has been released, a launched mass is accelerated towards a point of impact in a rearward direction.

FIGS. 4-7, for example, illustrate a perspective view of an orthopedic impacting tool in accordance with an embodiment of the present disclosure in which the motor and gearbox 8 of the mechanical spring assembly system rotates the cam 12 in a second direction (viewed as clockwise for tautological purposes), as shown by arrow 42b, and launches the mass or striker 15, in order to ultimately generate a rearward impact force. FIG. 4, and similarly FIG. 5, which is another perspective view of the impacting tool shown in FIG. 4 from an alternate angle, illustrates the cam 12 in mid-rotation. As the motor 8 continues to rotate the cam 12 in the second direction, a second spring piston 19b (hereinafter referred to as the "second piston 19b") engages a second spring 2b and is compressed against a second pusher plate 26b, thus storing potential energy within the second spring 2b. The second piston 19b, in turn, is "cocked" in the operative position ready for release (see FIG. 6). In the "cocking phase" the second piston 19b, in combination with the launched mass or striker 15, contacts and is pushed by the cam follower 13. As shown in FIGS. 6 and 7, for example, an end surface of the striker or launched mass 15 includes a pair of extensions or protrusions 32 integral with the launched mass 15 or provided as separate elements bolted to the launch mass 15. As the cam 12 continues to rotate in the second direction, energy stored inside the second spring 2b increases until the cam 12 moves past a release point where it ceases to act on the striker 15 (see FIG. 7, for example). The striker or launched mass 15 is now free to travel under the stored potential energy of the second spring 2b. In particular, after a sufficient displacement of the second piston 19b, and after the cam 12 releases the second piston 19b and/or the launched mass 15 combination, the second piston 19b moves in a rearward direction, i.e., a direction toward the point of impact, and, at the same time, accelerates the launched mass or striker 15, which is in contact with the face of the second piston 19b. As shown, for example, in FIG. 7, the second spring 2b releases from the striker 15, launching it away from the end of the tool that is proximate to the end effector or patient, with the extensions or protrusions 32 of the launched mass 15 impacting an alternate, second or rearward striking surface of the anvil 5, thereby percussively imparting a rearward impact force on the anvil 5.

Similar to the spring bumper 14a illustrated in FIG. 2 and discussed above, a spring bumper 14b shown in FIG. 4 also functions as a stopper to prevent an end face of the piston 19b from impacting the striker 15, as the piston 19b moves in the forward direction. The bumper 14b absorbs the impact of the piston 19b immediately before the launched mass or striker 15 is launched in the rearward direction. As discussed above, it was discovered in the course of the invention that without having the piston 19b come to rest on the bumper 14b, excessive wear occurred resulting in failure of the piston 19b. Accordingly, such bumper 14b prevents damage to the spring assembly system, particularly the piston 19b, during repeated operation. Similar to bumper 14a, the bumper 14b can be one of a plastic or more preferably a rubber or urethane material.

Figure 10:
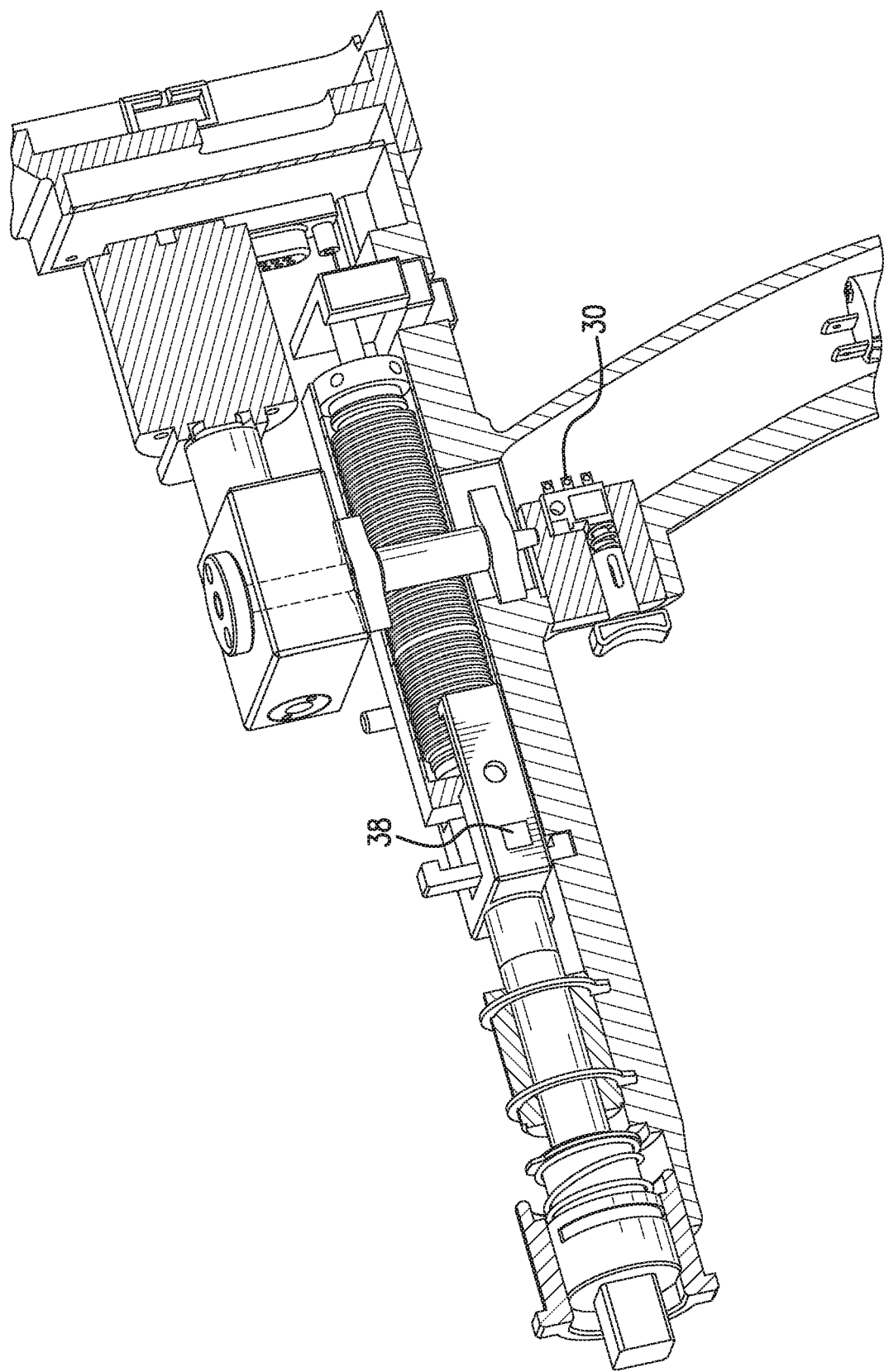
FIG. 10 shows an exemplary embodiment of the tool with a positional sensor used in determining the direction of impact.

In an exemplary embodiment, a direction of the force on the anvil 5 is controlled by the user's (such as a surgeon's) manual force on the tool detected by a sensor 28, which can be a positional sensor 38 on the anvil 5, as shown in FIG. 10. For example, biasing the tool in the forward direction results in the launched mass or striker 15 being launched forward and gives forward impacting, whereas biasing the tool in the rearward direction results in the striker 15 being launched rearward and gives rearward impacting.

In an embodiment, as the cam 12 assembly completes its stroke, it preferably activates a sensor 22, as shown, for example, in FIG. 5, coupled operatively to a controller 21. The sensor 22 assists in the regulation of the preferred cyclic operation of the cam 12. For example, the sensor 22 may signal the motor 8 to stop such that the cam 12 is at or near a point of minimal potential energy storage. Thus, in one complete cycle, a forward or a rearward impacting force may be applied on the broach, chisel, or other end effector, or on the implant or prosthesis. In a further embodiment, it may be advantageous to insert a delay or count the number of impacts for any give procedure before starting the next cycle, making it possible to accurately control the speed of impacting, and, in turn, allowing the surgeon to accurately control the rate of energy delivery in any given operation. In a still further embodiment, it may be advantageous to stop the cam 12 near a point of maximum potential energy storage to reduce a latency in the surgeons' hands. Latency, as defined, is the time between when the surgeon (or user) activates the orthopedic impacting tool and the tool actually delivers an impact. It has been determined by the inventor that latencies of around 100 milliseconds or less appear essentially as an instantaneous response. By stopping the cam 12 at a point where at least part of the potential energy has been stored, the tool has the effect of near instantaneous release of the potential energy upon actuation of a tool trigger 30.

In a further embodiment, an additional sensor 17 may be used to detect that the surgical implement is not progressing during the percussive impacting. FIG. 1 illustrates one possible location of the additional sensor 17. If the surgical implement has stopped advancing for a period of less than 10 seconds, or more preferably, less than 3 seconds, the tool can provide feedback to the surgeon. Such feedback may be provided in the form of lights, reduction or stoppage of the impacting, or other means. A surgeon will then have the opportunity to evaluate the procedure and determine whether to re-initiate the impacting operation.

Figure 8:
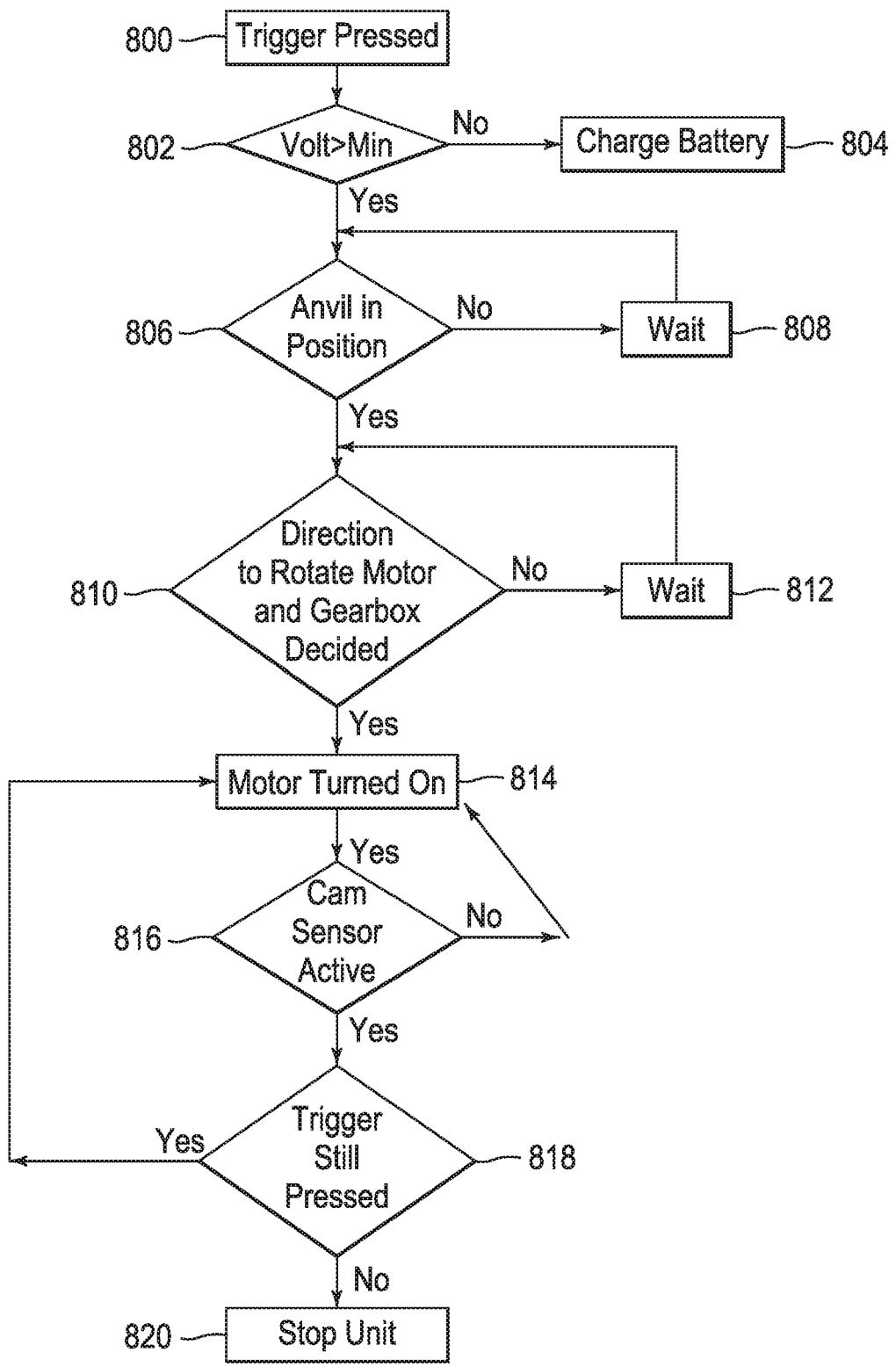
FIG. 8 is an exemplary flow chart illustrating a cyclic operation of the orthopedic impacting tool in accordance with an exemplary embodiment of the present disclosure.
Figure 9:
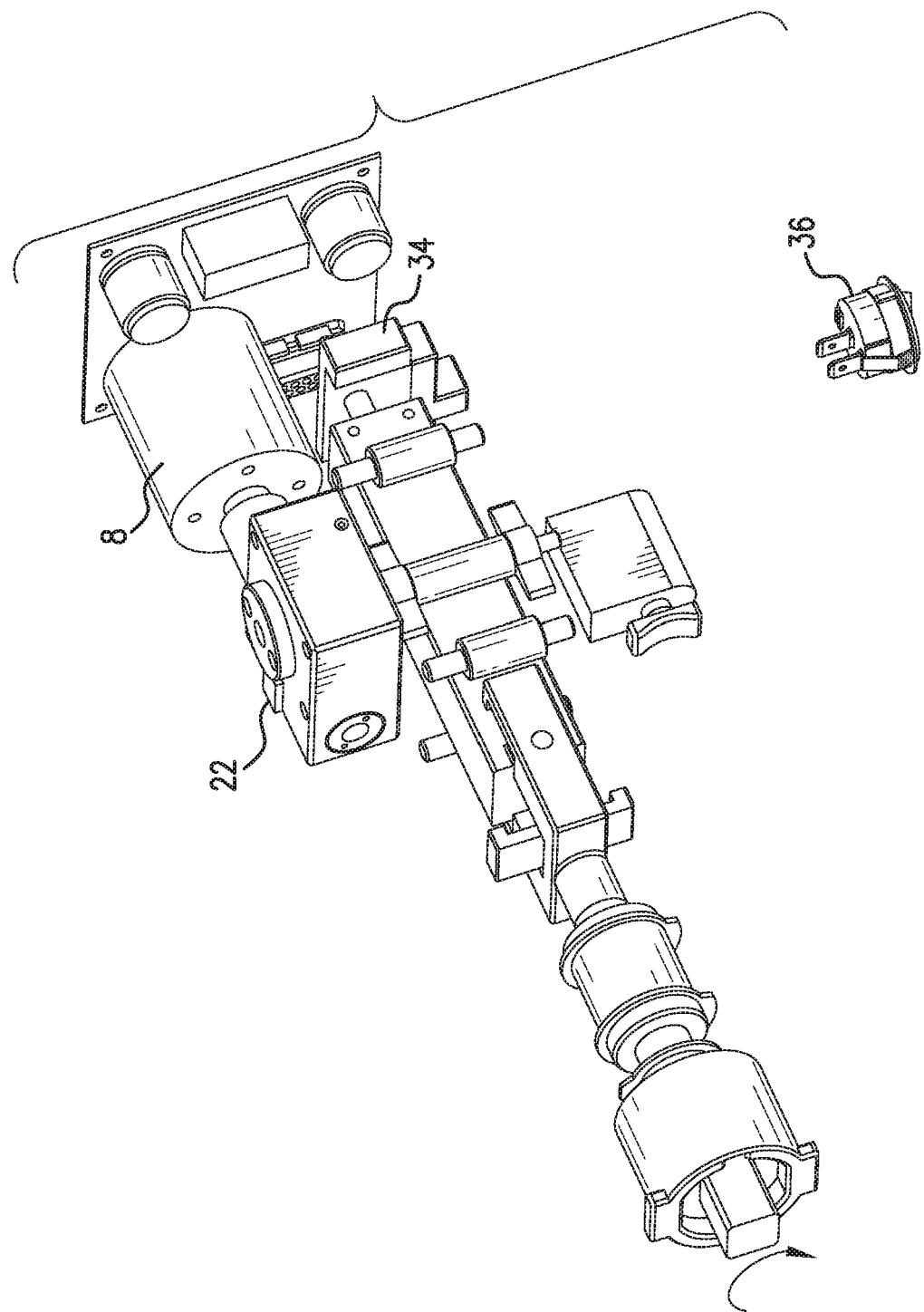
FIG. 9 shows an exemplary embodiment of the tool with mechanical switches used for controlling energy and frequency-related parameters.

FIG. 8 is an exemplary flow chart illustrating a cyclic operation of an orthopedic impacting tool according to an exemplary embodiment of the present disclosure. At the start of a cycle, a trigger is pressed in step 800 and it is first determined in step 802 whether the orthopedic impacting tool is charged and ready for use. If a voltage of a local power source, such as a battery, is less than a threshold minimum, then the battery is set to charge in step 804. If the voltage of the battery is greater than the threshold minimum, then it is next determined in step 806 whether an anvil and/or broach or other surgical attachment is correctly positioned relative to a cavity of the patient's bone. If the anvil and/or the broach or other surgical attachment is correctly positioned, the operation moves on to step 810; otherwise, the system waits until the position is corrected in step 808. Next, in step 810, it is determined whether a decision has been made as to which direction to rotate the motor and gearbox based on whether the tool is being used to generate a forward impact force or a rearward impact force. If the rotation direction has been decided, then the motor and gearbox combination starts rotating in step 814 in order to complete an impact cycle; otherwise, the system waits until the rotation direction has been determined in step 812. Once the motor gearbox completes an impact cycle, step 816 determines whether a cam sensor has been activated. If the sensor has been activated, then the process proceeds to step 818 to determine whether the trigger is still maintained; otherwise, the process returns to step 814 to allow the motor to continue rotating until the cam sensor has been activated. If a trigger is maintained in step 818, then the operation cycles back to step 814 where the motor continues to rotate, causing the tool to continue generating impacts; otherwise, the operation of the orthopedic impacting tool ceases at step 820.

The controller 21 preferably operates with firmware implementing the cyclic operation described in FIG. 8, which results in the orthopedic impacting tool being able to generate a repeatable, controllable impacting force. The controller 21 can include, for example, intelligent hardware devices, e.g., any data processor, microcontroller or FPGA device, such as those made by Intel® Corporation (Santa Clara, Calif.) or AMD® (Sunnyvale, Calif.). Other type of controllers can also be utilized, as recognized by those skilled in the art.

Advantageously, the piston and spring assembly system does not need or use a detent or a magnet for generating a higher energy impact. The magnitude of the energy output from the system is consistent for any given set of operating conditions, taking into consideration factors such as the spring constant, the spring preload force, and the total compression of the spring during the operational cycle. The impact energy output from the stored-energy drive system is between 1 to 10 joules, which varies no more than 20%, and preferably, no more than 10%, for a given operational cycle. For example, the impacting tool may include a spring with a spring constant of 100 pounds per inch, operating at a preload force of 100 pounds, and with a cam stroke of 0.5 inches, resulting in the stored-energy drive system outputting a total impact energy of about 7.1 joules, minus frictional and other losses.

In the present bidirectional impacting system the piston and spring assembly mechanism is approximately 80% efficient in the rearward direction compared to prior designs, which were about 20% efficient. For example, in the inventor's previous designs, a forward impact of approximately 3.5 J of energy would result in a rearward impact of only 0.4 J of energy, resulting in a loss of nearly 80% of the energy, which was not ideal.

It has been determined by the inventor that the mass ratios and materials used for the launched or thrown mass, the anvil, and the adapter are of critical importance in terms of the how effectively the kinetic energy of the thrown mass is conveyed to the surgical implement. For purposes of this invention, the ratio of the delivered energy to the surgical implement as a function of the kinetic energy in the thrown mass or striker is referred to as the transfer function. The transfer function is used as a measure of performance, in terms of how efficiently the tool is performing broaching, impacting, or extraction surgical procedures. For example, in one design in which the thrown mass, anvil, and adapter were all made of hardened stainless steel, the ratio of the energy conveyed to the surgical implement to the kinetic energy of the thrown mass, or the transfer function, was found to be less than 50%. By increasing the mass ratio of the thrown mass to the impacted mass (the sum of the mass of the anvil, the adapter, and the surgical implement), the efficiency of the system, in particular, the transfer function, was increased to greater than 60%, and in many cases, close to 75%.

Further, it was unexpectedly discovered that by keeping the compression ratio of the spring to less than 50% of its free length, and more preferably less than 30%, that spring life and impact consistency were maximized. One unexpected effect was generating much more consistent impacts between the striker 15 and the anvil 5, which was a result of the spring not permanently deforming. Indeed, the consistency of the impacts, as generated by the gas or mechanical spring, was found to be within +/−10% of the nominal design value since the impact energy was only slightly influenced by the environmental conditions.

The tool may further facilitate controlled continuous impacting, which impacting is dependent on a position of the trigger switch 30 operatively coupled to the power source or motor, for example. For such continuous impacting, after the trigger switch is activated, and depending on the position of the trigger switch 30, the tool may go through complete cycles at a rate proportional to the position of the trigger switch, for example. Thus, in either the single impact or continuous impacting operational modes, the creation or shaping of the surgical area is easily controlled by the surgeon.

As discussed previously, the tool is capable of varying the amount of impact energy per cycle by way of, for example, choosing an appropriate internal pressure for a replaceable gas spring cartridge (not shown) or a different mechanical spring for the stored-energy drive system. It will be appreciated that since the drive mechanism for imparting potential energy into the spring is a fixed stroke, different impact energies can be obtained in any given surgery by simply using a spring cartridge with a different preload or spring constant. In a further embodiment, an element, such as a linear cam, can be used to vary the amount of compression in the stored-energy drive system by changing a location of the pusher plate, for example. By controlling the impact energy the surgeon has greater flexibility during a procedure.

In a further embodiment, the tool may further be designed to facilitate extraction of well-fixed implants or "potted" broaches. Such embodiment rotates the cam 12 in the second, clockwise direction 42b and launches the mass or striker 15 such that the movement of the striker 15 is away from the patient, causing a retraction or rearward force on the anvil 5.

The tool may further include a compliance element (not shown) inserted between the striker 15 and the anvil 5. Preferably, the compliance element is a resilient material that recovers well from impact and imparts minimal damping on the total energy. As an example, a urethane component could be inserted at the interface where the striker 15 impacts the anvil 5. In a further embodiment, the compliance element may be inserted in such a fashion that it only reduces the impact force in the forward direction and does not affect the desire for a sharp impact force in the rearward direction. This type of compliance element can limit the peak force during impact to preclude such peaks from causing fractures in the patient's bone, yet maintain the high peak force necessary to be able to retract stuck broaches or other surgical implements.

In a still further embodiment, it is understood that the impactor could be coupled to a robot, for example, thus potentially eliminating the need for a portable power source (battery) and or hand grip on the tool.

In a further embodiment, the coupling of the adapter 1 to the tool may comprise a linkage arrangement or other adjustment mechanisms known in the art such that the position of the broach, chisel or other end effector can be modified without requiring the surgeon to rotate the tool. The orthopedic tool disclosed herein provides various advantages over the prior art. It facilitates controlled impacting at a surgical site, which minimizes unnecessary damage to a patient's body and allows precise shaping of an implant or prosthesis seat. The tool also allows the surgeon to modulate the direction, force, and frequency of the impacts, which improves the surgeon's ability to manipulate and control the tool. For example, the orthopedic tool can be used solely for retraction purposes depending on the surgical procedure being performed. Similarly, the tool can be customized to have different forward and reverse impact forces. In a mechanical spring assembly system, for example, different gauge springs can be used for forward and reverse impact. The force and compliance control adjustments of the impact settings allow a surgeon to set the force of impact according to a particular bone type or other profile parameter of a patient. Further, the improved efficiency and reduced linear motion converter loads allow use of smaller batteries and lower cost components. The tool thereby enables proper seating or removal of the prosthesis or implant into or out of an implant cavity. Further, the piston and spring assembly provides a simple means for adjusting the impact energy for a particular surgery. Additionally, since the spring assembly is essentially governed by the mechanical properties of the spring, such as the deflection, preload and spring constants, the resulting tool imparts a predictable impact energy independent of the operational speed. Furthermore, in one embodiment in which the gas spring cartridge is replaceable, elements subject to high wear, such as seals and pistons, can be replaced in each surgery, resulting in a more robust, long life tool and reducing points of failure.

Figure 11:
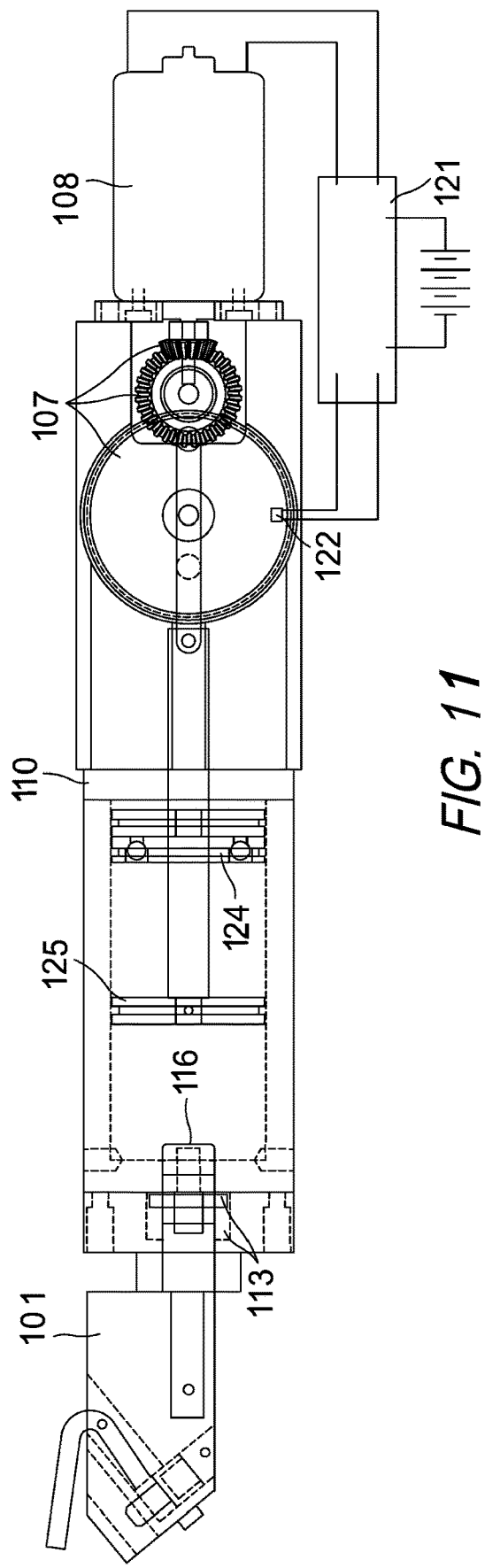
FIG. 11 shows an orthopedic impacting tool in accordance with another exemplary embodiment of the present disclosure.

Referring now to FIG. 11, in an exemplary embodiment, the linear motion converter 112 comprises a slider crank mechanism. The slider crank is operatively coupled, directly or indirectly, to the motor 108 and reducing gears 107. The tool further comprises a vacuum chamber 123 that accepts a piston 124 which may be actuated by the linear motion converter 112. It will be apparent that the piston 124 may be actuated in more than one direction. The vacuum is created in the vacuum chamber 123 by the movement of piston 124 away from striker 125. The vacuum created in the vacuum chamber 123 is defined as a pressure of less than about 9 psia for at least a portion of the operational cycle.

In an embodiment, the motor 108 causes the linear motion converter 112 to move, which pulls a vacuum on the face of the striker 125 and creates at least a partial vacuum in the vacuum chamber 123. The piston 124 continues to move increasing the size of the vacuum chamber 123 until it hits a forward portion of the striker 125 (i.e., a portion of the striker that is proximate to the end effector or patient), which dislodges the striker 125 from its detent 110 (for embodiments employing a detent) and allows it to rapidly accelerate towards the end of the tool that is proximate to the end effector or patient. The impact of the striker 125 on the anvil 114 communicates a force to the adapter 101 and the broach, chisel or other orthopedic instrument.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The exemplary embodiment was chosen and described in order to best explain the principles of the present disclosure and its practical application, to thereby enable others skilled in the art to best utilize the disclosure and various embodiments with various modifications as are suited to the particular use contemplated.

What is claimed is:

1. A surgical impacting tool, comprising:
a mechanical spring configured to release energy stored therein to drive an operably linked surgical implement;
a cam configured to rotate and thereby cause energy to be stored in the mechanical spring;
a motor configured to drive the rotation of the cam;
an electronic controller configured to control the motor and monitor and manage storage and release of the energy of the mechanical spring;
an adapter configured to secure to the surgical implement;
a mass configured to deliver an impact force responsive to the released energy to the surgical implement secured to the adapter to advance the surgical implement relative to a surgical target; and
a sensor operatively connected to the controller and configured to sense whether the surgical implement has not advanced in response to the delivered impact force, wherein the controller is configured to cause feedback to be provided to a user of the tool in response to the sensor sensing that the surgical implement has not advanced in response to the delivered impact force.

2. The surgical impacting tool of claim 1, further comprising:
an anvil,
wherein the mass is operable to impact the anvil.

3. The surgical impacting tool of claim 1, further comprising an energy adjustment mechanism configured to adjust the energy released in accordance with a patient profile.

4. The surgical impacting tool of claim 1, wherein an impact energy delivered per impact is constant.

5. The surgical impacting tool of claim 1, wherein the mass has an axial orientation no more than 10 degrees offset from an axis of the adapter.

6. The surgical impacting tool of claim 1, wherein the adapter is configured to communicate at least 60% of an impact energy to the surgical implement.

7. The surgical impacting tool of claim 1, further comprising at least one timing element configured to time a length of each impacting cycle of a plurality of impacting cycles during continuous impacting, wherein the controller is configured to receive feedback from the at least one timing element and to manage storage and release of the energy based in part on the at least one timing element.

8. The surgical impacting tool of claim 1, wherein a variance of energy released across a plurality of impacting cycles is at most 20%.

9. The surgical impacting tool of claim 1, wherein the mechanical spring is configured to release the energy stored therein at a rate of between 1 to 10 times per second to drive the operably linked surgical implement.

10. The surgical impacting tool of claim 1, wherein the energy is released at a rate of between 3 and 30 joules per second.

11. The surgical impacting tool of claim 1, further comprising a cam follower operatively coupled to the cam; and
a piston operatively coupled to the cam follower such that the rotation of the cam is configured to cause the cam follower to push the piston and thereby compress the mechanical spring to store energy in the mechanical spring.

12. The surgical impacting tool of claim 11, wherein the stored energy is configured to be released from the mechanical spring in response to the cam follower ceasing to push the piston.

13. The surgical impacting tool of claim 1, wherein the mechanical spring includes a single mechanical spring.

14. A surgical impacting tool, comprising:
a cam;
a cam follower configured to move in response to being driven by the cam;
a mechanical spring operatively connected to the cam follower, the mechanical spring being configured to store energy therein in response to the movement of the cam follower and to release energy therefrom in response to the movement of the cam follower;
a motor configured to drive movement of the cam;
an electronic controller configured to control the motor and thereby the movement of the cam and thereby control storage and release of the energy from the mechanical spring;
an adapter configured to secure to a surgical implement;
a mass configured to deliver an impact force responsive to the released energy to the surgical implement secured to the adapter; and
a sensor operatively connected to the controller and configured to sense whether the surgical implement has not advanced in response to the delivered impact force, wherein:
the controller is configured to cause feedback to be provided to a user of the tool in response to the sensor sensing that the surgical implement has not advanced in response to the delivered impact force, and
the feedback includes at least one of a light, a reduction in the release of energy from the spring, and a stoppage in the release of energy from the spring.

15. The surgical impacting tool of claim 14, wherein the movement of the cam comprises rotational movement, the storage of energy comprises compression of the mechanical spring, and the release of energy comprises decompression of the mechanical spring.

16. The surgical impacting tool of claim 14, wherein the controller is configured to control cyclic movement of the mass such that the mass repeatedly moves and repeatedly delivers the impact force.

17. The surgical impacting tool of claim 14, wherein the mechanical spring includes a coil spring.

* * * * *